United States Patent
Thompson (10) Patent No.: US 9,999,529 B2
(45) Date of Patent: Jun. 19, 2018

(54) HOLLOW DRUG-FILLED STENT AND METHOD OF FORMING HOLLOW DRUG-FILLED STENT

(71) Applicant: Medtronic Vascular, Inc., Santa Rosa, CA (US)

(72) Inventor: Dustin Thompson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days. days.

(21) Appl. No.: 14/809,718

(22) Filed: Jul. 27, 2015

(65) Prior Publication Data
US 2015/0328023 A1 Nov. 19, 2015

Related U.S. Application Data

(62) Division of application No. 13/360,538, filed on Jan. 27, 2012, now Pat. No. 9,119,736.

(51) Int. Cl.
*A61F 2/06* (2013.01)
*A61F 2/86* (2013.01)
(Continued)

(52) U.S. Cl.
CPC .................. *A61F 2/86* (2013.01); *A61F 2/82* (2013.01); *A61L 31/022* (2013.01); *A61L 31/16* (2013.01);
(Continued)

(58) Field of Classification Search
CPC . A61F 2/91; A61F 2/915; A61L 31/06; A61L 31/18
See application file for complete search history.

(56) References Cited

U.S. PATENT DOCUMENTS

| 4,800,882 A | 1/1989 | Gianturco |
| 4,886,062 A | 12/1989 | Wiktor |

(Continued)

FOREIGN PATENT DOCUMENTS

| WO | WO2008/036380 | 3/2008 |
| WO | WO2012/036875 | 3/2012 |
| WO | WO2012/036890 | 3/2012 |

OTHER PUBLICATIONS

U.S. Appl. No. 13/190,775, filed Jul. 26, 2011, Thompson.

*Primary Examiner* — Thomas J Sweet
*Assistant Examiner* — Tiffany Shipmon
(74) *Attorney, Agent, or Firm* — Medler Ferro Woodhouse & Mills PLLC (57) ABSTRACT

A stent is formed from a wire that in cross-section includes an outer member having a lumen and a radiopaque core member partially filling the lumen. A substance for elution through openings formed through the outer member fills the portion of the lumen not filled by the radiopaque core member. In a method of forming the stent, a composite wire including an outer member and a dual core member is shaped into a stent pattern. The dual core member includes a first core member and a second, radiopaque core member. The shaped composite wire is processed to remove the first core member from the outer member without adversely affecting the outer member and the second core member. The portion of the lumen that was occupied by the first core member may be filled with a substance for elution through openings from through the outer member to the lumen.

22 Claims, 3 Drawing Sheets

(51) Int. Cl.
  *A61F 2/82* (2013.01)
  *A61L 31/16* (2006.01)
  *A61L 31/02* (2006.01)
  *A61L 31/18* (2006.01)

(52) U.S. Cl.
  CPC ......... *A61L 31/18* (2013.01); *A61F 2240/001* (2013.01); *A61F 2250/0068* (2013.01); *A61F 2250/0098* (2013.01)

(56) References Cited

U.S. PATENT DOCUMENTS

| | | | |
|---|---|---|---|
| 5,019,090 A | 5/1991 | Pinchuk | |
| 5,133,732 A | 7/1992 | Wiktor | |
| 5,630,840 A | 5/1997 | Mayer | |
| 5,782,903 A | 7/1998 | Wiktor | |
| 6,071,305 A * | 6/2000 | Brown | A61F 2/82 606/191 |
| 6,136,023 A | 10/2000 | Boyle | |
| 6,248,190 B1 | 6/2001 | Stinson | |
| 6,364,902 B1 * | 4/2002 | Dickenson | A61F 2/91 623/1.15 |
| 6,379,381 B1 | 4/2002 | Hossainy et al. | |
| 6,497,709 B1 | 12/2002 | Heath | |
| 7,101,392 B2 | 9/2006 | Heath | |
| 7,250,043 B2 * | 7/2007 | Chan | A61L 29/16 604/264 |
| 8,381,774 B2 | 2/2013 | Mitchell et al. | |
| 8,460,745 B2 | 6/2013 | Mitchell et al. | |
| 2005/0060861 A1 * | 3/2005 | Bradley | B21C 1/003 29/423 |
| 2006/0292077 A1 | 12/2006 | Zhao | |
| 2008/0300673 A1 | 12/2008 | Clerc et al. | |
| 2009/0132031 A1 | 5/2009 | Cook et al. | |
| 2010/0152837 A1 | 6/2010 | Lundkvist | |
| 2010/0191318 A1 | 7/2010 | Stinson et al. | |
| 2010/0269950 A1 | 10/2010 | Hoff et al. | |
| 2011/0008405 A1 | 1/2011 | Birdsall et al. | |
| 2011/0067778 A1 * | 3/2011 | Mitchell | A61L 31/16 141/1 |
| 2011/0070358 A1 | 3/2011 | Mauch et al. | |
| 2011/0251668 A1 | 10/2011 | Thompson et al. | |
| 2012/0067103 A1 * | 3/2012 | Bienvenu | A61F 2/88 72/369 |
| 2012/0067454 A1 | 3/2012 | Melder | |
| 2012/0067455 A1 | 3/2012 | Mitchell et al. | |
| 2012/0070562 A1 | 3/2012 | Avelar et al. | |
| 2012/0070563 A1 | 3/2012 | Mitchell et al. | |
| 2013/0025339 A1 | 1/2013 | Costa et al. | |

* cited by examiner

HOLLOW DRUG-FILLED STENT AND METHOD OF FORMING HOLLOW DRUG-FILLED STENT

RELATED APPLICATIONS

This application is a Division of and claims the benefit of U.S. patent application Ser. No. 13/360,538 filed Jan. 27, 2012, now allowed. The disclosures of which are herein incorporated by reference in their entirety.

FIELD OF THE INVENTION

The present invention relates hollow drug-filled stents and methods of forming hollow-drug-filled stents, and in particular, hollow-drug filled stents with improved radiopacity.

BACKGROUND OF THE INVENTION

Drug-eluting implantable medical devices such as stents have become popular in recent times for their ability to perform their primary function (such as structural support) and their ability to medically treat the area in which they are implanted.

For example, drug-eluting stents have been used to prevent restenosis in coronary arteries. Drug-eluting stents may administer biologically or pharmacologically active substances such as anti-inflammatory compounds that block local invasion/activation of monocytes, thus preventing the secretion of growth factors that may trigger VSMC proliferation and migration. Other potentially anti-restenotic compounds include anti-proliferative agents, such as chemotherapeutics, which include rapamycin and paclitaxel. Other classes of drugs such as anti-thrombotics, anti-oxidants, platelet aggregation inhibitors and cytostatic agents have also been suggested for anti-restenotic use.

Drug-eluting medical devices may be coated with a polymeric material which, in turn, is impregnated with a biologically or pharmacologically active substance or a combination of biologically or pharmacologically active substances. Once the medical device is implanted at a target location, the biologically or pharmacologically active substance is released from the polymer for treatment of the local tissues. The biologically or pharmacologically active substance is released by a process of diffusion through the polymer layer for biostable polymers, and/or as the polymer material degrades for biodegradable polymers.

Controlling the rate of elution of a biologically or pharmacologically active substance from the impregnated polymeric material is generally based on the properties of the polymer material. However, at the conclusion of the elution process, the remaining polymer material in some instances has been linked to an adverse reaction with the vessel, possibly causing a small but dangerous clot to form. Further, drug impregnated polymer coatings on exposed surfaces of medical devices may flake off or otherwise be damaged during delivery, thereby preventing the biologically or pharmacologically active substance from reaching the target site. Still further, drug impregnated polymer coatings are limited in the quantity of the biologically or pharmacologically active substance to be delivered by the amount of a drug that the polymer coating can carry and the size of the medical devices. Controlling the rate of elution using polymer coatings is also difficult.

Accordingly, stents with hollow, drug-filled structural members have also been contemplated. For example, U.S. Pat. No. 6,071,305 to Brown et al. generally discloses a stent formed of an elongated member in a spiral tube configuration. The elongated member includes a groove that can be filled with an active agent. Further, U.S. Application Publication No. 2011/0008405 to Birdsall et al. and U.S. Application Publication No. 2011/0070358 to Mauch et al., each of which is incorporated by reference herein in its entirety, describe methods of forming stents with hollow-drug-filled structural members from composite wires. However, preferred structural members for stents, such as nickel-titanium alloys ("nitinol") and alloys of cobalt, nickel, chromium and molybdenum ("MP35N", "MP20N") are relatively radiolucent, especially when hollow. Thus, there is a need for a stent with hollow-drug filled structural members with improved radiopacity.

SUMMARY OF INVENTION

Embodiments hereof relate to a stent with hollow, drug filled struts and crowns. The struts and crowns are formed from a wire. The wire includes an outer member or shell and a lumen. A portion of the lumen is filled with a radiopaque material continuously along the length of the wire. In one embodiment, the overall lumen is generally circular and the radiopaque material is generally D-shaped, thereby leaving a generally D-shaped open lumen that may be filled with a biologically or pharmacologically active agent.

Embodiments hereof also relate to a method of forming a stent. A composite wire including an outer member and a dual core member disposed within the lumen of the outer member is shaped into a stent pattern. The dual core member includes a first core member and a second core member. The shaped composite wire is processed such that the first core member is removed from the lumen of the outer member without adversely affecting the outer member and the second core member, such as by chemical etching. Openings may be provided through the outer member to the lumen of the outer member before or after the processing step. The portion of the lumen where first core member was removed may be filled with a biologically or pharmacologically active substance to be eluted through the openings provided through the outer member.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, where like reference numbers indicate identical or functionally similar elements.

Figure 1:
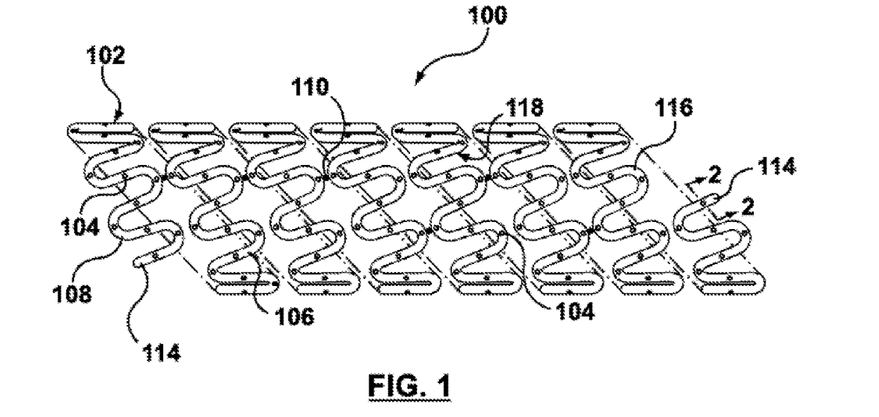
FIG. 1 is a schematic illustration of an exemplary stent in accordance with an embodiment hereof.
Figure 2:
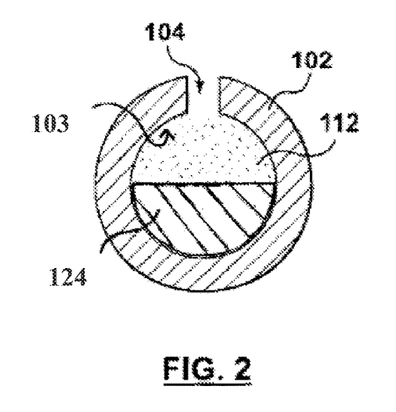
FIG. 2 is a cross-sectional view taken along line 2-2 of FIG. 1.
Figure 3:
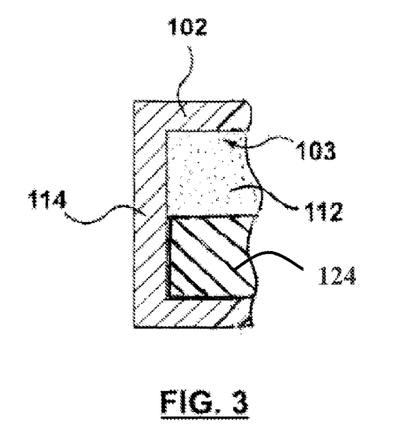
FIG. 3 is a longitudinal cross-section of an end of the wire of the stent of FIG. 1.
Figure 4:
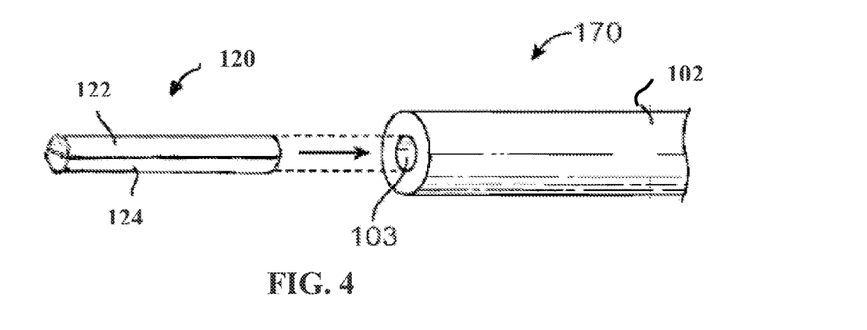
FIG. 4 is a schematic illustration of a composite wire including an outer member, a first core member, and a second core member.

An embodiment of a stent 100 disclosed herein is shown in FIGS. 1-3. In particular, stent 100 is formed from a hollow wire 102, wherein a lumen 103 of the hollow wire 102 is partially filled with a radiopaque core member 124. The term "wire" as used herein means an elongated element or filament or group of elongated elements or filaments and is not limited to a particular cross-sectional shape or material, unless so specified. In the embodiment shown in FIG. 1, hollow wire 102 is formed into a series of generally sinusoidal waveforms including generally straight segments or struts 106 joined by bent segments or crowns 108 and the waveform is helically wound to form a generally tubular stent 100. In the embodiment shown in FIG. 1, selected crowns 108 of longitudinally adjacent sinusoids may be joined by, for example, fusion points 110. The invention hereof is not limited to the pattern shown in FIG. 1. Wire 102 of stent 100 can be formed into any pattern suitable for use as a stent. For example, and not by way of limitation, wire 102 of stent 100 can be formed into patterns disclosed in U.S. Pat. No. 4,800,882 to Gianturco, U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety. Further, instead of a single length of wire formed into a stent pattern, a plurality of wires may be formed into a two-dimensional waveform and wrapped into individual cylindrical elements. The cylindrical elements may then be aligned along a common longitudinal axis and joined to form the stent.

As shown in FIG. 2, hollow wire 102 of stent 100 includes a radiopaque core member 124 that occupies a portion of the lumen 103 of hollow wire 102. Radiopaque core member 124 allows stent 100 to be visible under X-ray or fluoroscopic imaging equipment when outer member 102, described below, is made of a material that is not sufficiently radiopaque to be visible under X-ray or fluoroscopic imaging equipment. Thus radiopaque core member 124 is more radiopaque than outer member 102. The term "radiopaque" refers to the ability of a substance to absorb or attenuate X-rays. Few substances will transmit 100% of X-rays and few substances will absorb 100% of X-rays. For the purposes of this disclosure, radiopaque will refer to those substances or materials which are capable of being imaged by an X-ray imaging device such as but not limited to a fluoroscope. The remaining portion of lumen 103 allows for a biologically or pharmacologically active substance 112 to be deposited there within. Although hollow wire 102 is shown as generally having a circular cross-section, hollow wire 102 may be generally elliptical or rectangular in cross-section. Hollow wire 102 further includes cuts or openings 104 dispersed along its length to provide access to lumen 103 to permit biologically or pharmacologically active substance 112 to be released from lumen 103. Openings 104 may be disposed only on struts 106 of stent 100, only on crowns 108 of stent 100, or both struts 106 and crowns 108. Openings 104 may be sized and shaped as desired to control the elution rate of biologically or pharmacologically active substance 112 from stent 100. Larger sized openings 104 generally permit a faster elution rate and smaller sized openings 104 generally provide a slower elution rate. Further, the size and/or quantity of openings 104 may be varied along stent 100 in order to vary the quantity and/or rate of biologically or pharmacologically active substance 112 being eluted from stent 100 at different portions of stent 100. Openings 104 may be, for example and not by way of limitation, 5-30 µm in diameter. Openings 104 are provided to access the portion of lumen 103 with biologically or pharmacologically active substance and may be provided on an outwardly facing or abluminal surface 116 of stent 100, as shown in FIG. 2, or on the inwardly facing or luminal surface 118 of stent 100, or may be provided anywhere along the circumference of wire 102 provide that the openings 104 provide access to the portion of lumen 103 with biologically or pharmacologically active substance 112. Openings 104 may have a constant diameter through the depth or have a tapered or conical shape.

Ends 114 of wire 102 may be closed, as shown in FIG. 3. Ends 114 may be closed by crimping excess material of wire 102 to close lumen 103. Closing ends 114 prevents biologically or pharmacologically active substance 112 from prematurely releasing from ends 114. However, closing ends 114 is not required as substance 112 may be dried, provided within a polymer matrix, enclosed within a liner (not shown), or otherwise protected from premature release from ends 114. Further, ends 114 may be welded, crimped or otherwise connected to other portions of wire 102 such that the ends 114 are not free ends. Ends 114 may alternatively be provided as free ends.

Figure 5:
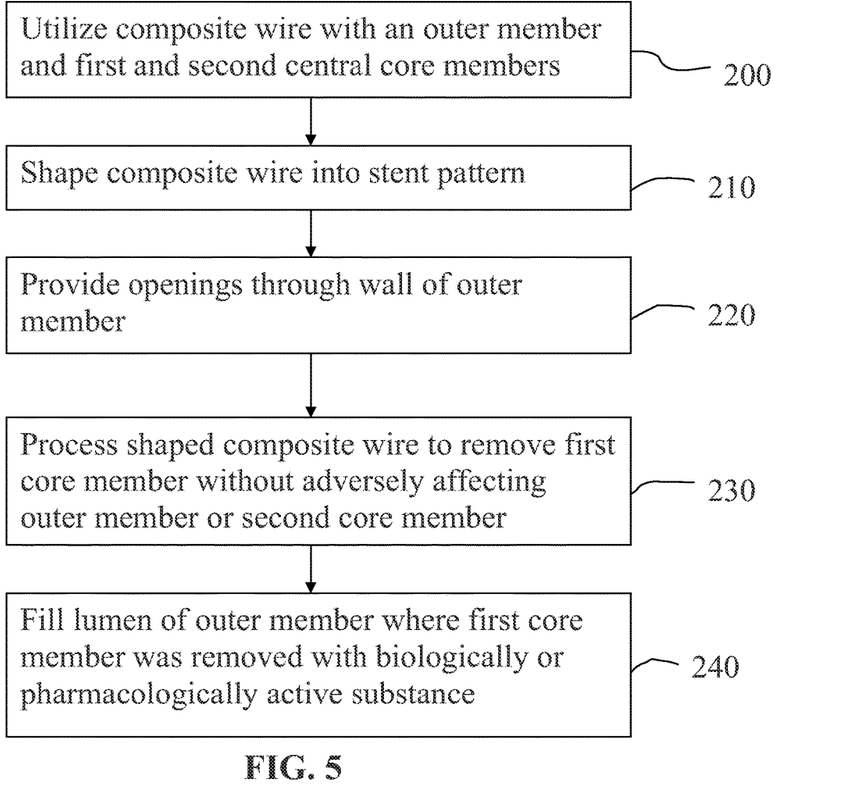
FIG. 5 is flow chart illustrating an embodiment of a method of forming a hollow wire stent including a radiopaque core.

FIGS. 4-9 show a method for forming a hollow wire stent in accordance with an embodiment hereof. As shown in FIG. 5, step 200 is to utilize a composite wire 170 having an outer member 102 and a dual core member 120 disposed within a lumen 103 of outer member 102, as shown schematically in FIG. 4. Dual core member 120 is formed from a first core member 122 and a second core member 124. Outer member 102 becomes hollow wire 102 of stent 100, and thus has been labeled with the same reference number. Second core member 124 is formed from a radiopaque material and becomes radiopaque core member 124 shown in FIGS. 2-3. Composite wire 170 may be formed by any method known in the art, for example and not by way of limitation, a drawn filled tubing process, extrusion, or any other suitable method. In one example, first and second core members may 122, 124 may each be machined into a D-shaped or semi-circular cross-section from a respective rod. The flat sides of the D-shaped first and second core members may be placed side by side to form a cylindrical rod. The dual core member 120 may then be encapsulated by outer member 102, such as by methods of forming composite wires known to those skilled in the art. Examples of composite wires and methods of forming composite wires can be found in U.S. Pat. No. 5,630,840 to Mayer, U.S. Pat. No. 6,248,190 to Stinson, U.S. Pat. No. 6,497,709 to Heath, and U.S. Pat. No. 7,101,392 to Heath, each of which is incorporated by reference herein in its entirety.

Outer member 102 may be any material that is suitable to be used as a stent, provided that it survives the process of removing first core member 122, as described in more detail below. For example and not by way of limitation, outer member 102 may be a stainless steel, "MP35N," "MP20N," nickel titanium alloys such as Nitinol, magnesium, L605, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The requirements for the material of outer member 102 are that it be biocompatible, sufficiently resilient to be used as a stent, and that it survives the process for eliminating first core member 122, as discussed in more detail below.

First core member 122 and second core member 124 may be made of materials that have a similar stiffness, such that their geometries are similar after processing to form composite member 170 and to shape composite member into a stent form, as described in more detail below. Further, second core member 124 is made of a radiopaque material that survives the process for removing first core member 122. In a non-limiting example, outer member 102 is made of MP35N, first core member 122 is made of tantalum, and second core member 124 is made of a platinum-iridium alloy such as Pt10Ir or Pt20Ir. Pt10Ir is a platinum-iridium alloy containing about 90% platinum by weight and about 10% iridium by weight. Similarly, Pt20Ir is a platinum-iridium alloy containing about 80% platinum by weight and about 20% iridium by weight. Other examples of material combinations of outer member 102, first core member 122 (sacrificial material), second core member 124 (survivor radiopaque material), and an etchant as described in detail below, include, but are not limited to those listed in the following table:

| Outer Member Material | Etchant | First Core Member (sacrificial material) | Second Core Member (survivor material) |
| --- | --- | --- | --- |
| MP35N, L605, Nitinol | XeF$_2$ | tantalum, tungsten, molybdenum, niobium, rhenium, carbon, germanium, silicon | platinum, platinum-iridium alloys |
| MP35N, L605, 316L, tantalum, tungsten, molybdenum, molybdenum-rhenium alloy | high temperature | silver, copper, aluminum | tantalum, tungsten, platinum, platinum-iridium alloys |
| Stainless Steel | nitric acid | copper | platinum, platinum-iridium alloys |

Figure 6:
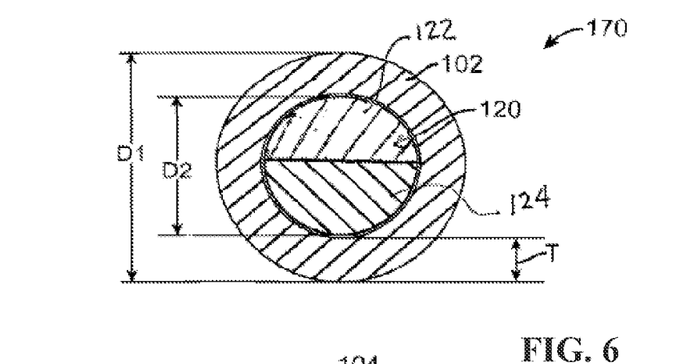
FIGS. 6-9 are cross-sectional views of the composite wire of FIG. 4 at various stages of the method of FIG. 5.

A cross-section of composite wire 170 is shown in FIG. 6. Outer member 102 may have an outer diameter D1 in the range of 0.0025 inch to 0.010 inch and wall thickness T in the range of 0.0005 inch or larger, depending on the application, for example, in what lumen or organ and for what purpose the stent is to be utilized. Accordingly, dual core member 120 may have an outer diameter of 0.0002 inch to 0.0095 inch. The values listed above are merely examples and other diameters and thicknesses may be used depending on, for example, the materials used, the desired stent shape, and the purpose or location of the stent.

Referring back to FIG. 5, step 210 is to shape the composite wire 170 into the stent pattern. As discussed above, the stent pattern can be the pattern shown in FIG. 1 or any other suitable pattern formed from a wire. Further, although the order of all the steps is not critical, step 210 should be done prior to removing first core member 122, as explained in more detail below. However, the step of shaping the composite member 170 into the stent pattern does not have to include shaping composite member 170 into the final stent pattern. For example, the step 210 of shaping the composite member 170 into a stent pattern may include only forming the struts 106 and crowns 108 in composite wire 170. Shaping composite wire 170 into the stent pattern while dual core member 120 is disposed within outer member 102 helps prevent kinking or other deformations from occurring in outer member 102. Shaping the composite wire 170 into the stent pattern shown in FIG. 1 generally includes the steps of forming composite wire 170 into a two dimensional waveform pattern followed by wrapping the pattern around a mandrel, as known to those skilled in the art. The end result is a helical stent pattern formed onto a mandrel. Selected crowns 108 of the helical pattern may then be fused together and the stent may be removed from the mandrel. Step 210 of shaping composite wire 170 into the stent pattern can be performed with techniques known to those skilled in the art. For example, and not by way of limitation, forming the composite wire 170 into a two dimensional waveform can be achieved using techniques described in U.S. Application Publication Nos. 2010/0269950 to Hoff et al. and 2011/0070358 to Mauch et al., and co-pending U.S. application Ser. Nos. 13/191,134 and 13/190,775, filed Jul. 26, 2011, each of which is incorporated in its entirety by reference herein. Other techniques known to those skilled in the art could also be used.

Figure 7:
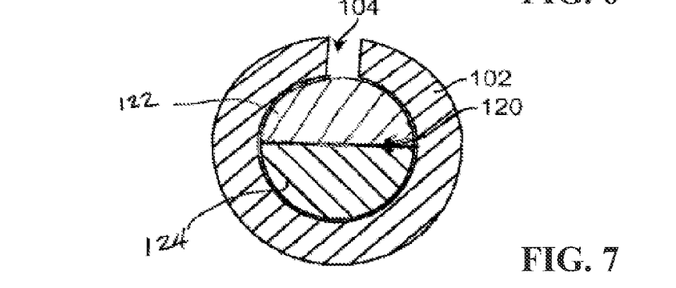
Figure 8:
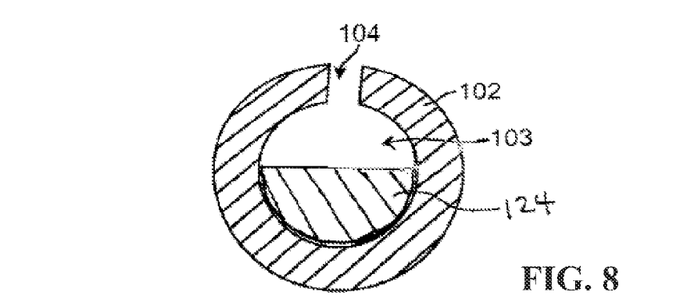

Step 220 shown in FIG. 5 is to provide openings 104 in outer member 102. Openings 104 may be laser cut, drilled, etched, or otherwise provided in outer member 102. Step 220 need not be performed after step 210, nor before step 230, although it is preferred to be before step 230, as explained in more detail below. If step 220 is performed after step 210, a cross-section of composite wire 170 will include outer member 102, dual core member 120, and an opening 104, as shown in FIG. 7.

Step 230 is to remove first core member 122 from lumen 103 of outer member 102 without adversely affecting outer member 102 or second core member 124, such as by chemical etching. Step 230 can be performed by any suitable process for removing first core member 122 while preserving outer member 102 and second core member 124. In particular, exposing composite wire 170 to xenon difluoride (XeF$_2$) gas at low pressure 1-6 Torr and relatively high temperature (approximately 150° C.) causes the xenon difluoride (XeF$_2$) gas to react with a tantalum (Ta) first core member 122 to form TaF$_5$ and Xe gases, which can be exhausted from lumen 103. Xenon difluoride (XeF$_2$) gas reacts similarly with a first core member 120 made from tungsten, molybdenum, niobium, rhenium, carbon, germanium, and silicon. However, xenon difluoride (XeF$_2$) gas does not react with an outer member 102 formed of MP35N or a second core member 124 formed of platinum-iridium alloys such as Pt20Ir and Pt10Ir described above, or other materials including, but not limited to, those materials listed in the table above. Accordingly, after step 230 is completed, outer member 102 and second core member 124 remain, and first core member 122 has been removed, leaving the cross-sectional structure shown in FIG. 8. As noted above, openings 104 do not need to be formed prior to the step of removing first core member 122 as long as there is a way to expose first core member 122 to the etchant. For example, ends 114 of the wire may be open or temporary ports may for formed through outer member 102 to expose first core member 122 to the etchant.

Although a particular embodiment of an outer member 102 made from MP35N, a first core member 122 made from tantalum, a second core member 124 made from a platinum-iridium alloy, and a xenon difluoride etchant has been described, those skilled in the art would recognize other combinations of materials and etchants that could be utilized. For example, and not by way of limitation, the material and etchant/removal process combinations listed in the table above may be used. The description in the table of the etchant as "high temperature" comprises exposing the composed wire to a temperature high enough to melt the material of the first core member 122 but not sufficiently high to melt the material of the outer member 102 or the second core member 124. Further, other materials and methods for removing core members may used, as described, for example, in U.S. Application Publication No. 2011/0008405 to Birdsall et al. and U.S. Application Publication No. 2011/0070358 to Mauch et al., each of which is incorporated by reference herein in its entirety.

Figure 9:
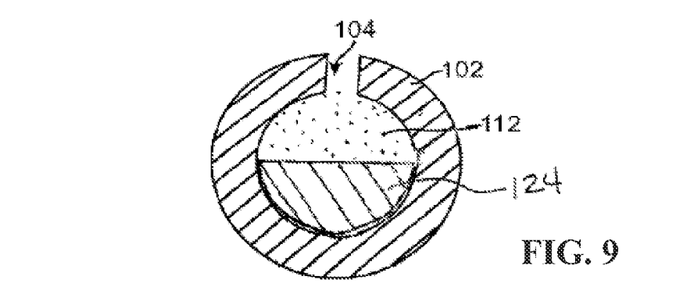

After first core member 122 has been removed, biologically or pharmacologically active substance 112 may be injected into lumen 103 of outer 102, as shown in step 240 of FIG. 5. This produces a hollow wire or outer member 102 with a radiopaque core member 124 partially filling the lumen 103 of the outer member 102 and biologically or pharmacologically active substance 112 filling the portion of the lumen 103 not occupied by the radiopaque core member, and openings 104 through which biologically or pharmacologically active substance 112 may be eluted, as shown in FIGS. 2 and 9. Filling lumen 103 with a biologically or pharmacologically active substance may be accomplished by any means known to those skilled in the art. For example, and not by way of limitation, methods for filling lumens of hollow wires described in U.S. Application Publication No. 2011/0070357 to Mitchell et al., which is incorporated by reference herein in its entirety; and co-pending U.S. application Ser. Nos. 12/884,362; 12/884,451; 12/884,501; 12/884,578; 12/884,596 each filed on Sep. 17, 2010, and each of which is incorporated by reference herein in its entirety.

The biologically or pharmacologically active substance 112 may include, but is not limited to, antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include ABT-578 (a synthetic analog of rapamycin), rapamycin (sirolimus), zotarolimus, everolimus, angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other biologically or pharmacologically active substances or agents that may be used include nitric oxide, alpha-interferon, genetically engineered epithelial cells, and dexamethasone. In other examples, the biologically or pharmacologically active substance is a radioactive isotope for implantable device usage in radiotherapeutic procedures. Examples of radioactive isotopes include, but are not limited to, phosphorus ($P^{32}$), palladium ($Pd^{103}$), cesium ($Cs^{131}$), Iridium ($I^{192}$) and iodine ($I^{125}$). While the preventative and treatment properties of the foregoing biologically or pharmacologically active substances are well-known to those of ordinary skill in the art, the biologically or pharmacologically active substances are provided by way of example and are not meant to be limiting. Other biologically or pharmacologically active substances are equally applicable for use with the disclosed methods and compositions.

Further, a carrier may be used with the biologically or pharmacologically active substance. Examples of suitable carriers include, but are not limited to, ethanol, acetone, tetrahydrofuran, dymethylsulfoxide, a combination thereof, or other suitable carriers known to those skilled in the art. Still further, a surfactant may be formulated with the biologically or pharmacologically active substance and the solvent to aid elution of the biologically or pharmacologically active substance.

Stent 100 may be used conventionally in blood vessels of the body to support such a vessel after an angioplasty procedure. It is known that certain biologically or pharmacologically active substances eluted from stents may prevent restenosis or other complications associated with angioplasty or stents. Stent 100 may alternatively be used in other organs or tissues of the body for delivery of biologically or pharmacologically active substance to treat tumors, inflammation, nervous conditions, or other conditions that would be apparent to those skilled in the art.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. A method of forming a stent comprising the steps of:
shaping a composite wire into a stent pattern, wherein the composite wire comprises an outer member and a dual core member disposed within a lumen of the outer member, wherein the dual core member comprises a first core member disposed within a first portion of the lumen and a second core member disposed within a second portion of the lumen, wherein the first core member and the second core member are disposed side-by-side in an abutting relationship within the lumen of the outer member;

processing the composite wire such that the first core member is removed from the lumen of the outer member without adversely affecting the outer member and the second core member, wherein the processing step occurs prior to placement of the stent within a body.

2. The method of claim 1, wherein the second core member comprises a radiopaque material.

3. The method of claim 2, further comprising the step of filling the first portion of the lumen of the outer member with a biologically or pharmacologically active substance.

4. The method of claim 1, further comprising the step of providing openings through the outer member to the first portion of the lumen of the outer member.

5. The method of claim 1, wherein the outer member is formed from MP35N, the first core member is formed from tantalum, and the second core member is formed from a platinum iridium alloy, wherein the step of processing the composite wire to remove the first core member comprises exposing the composite wire to a xenon difluoride gas.

6. The method of claim 1, wherein the outer member is formed from a material selected from the group consisting of MP35N, L605, 316L stainless steel, the first core member is formed from a material selected from the group consisting of silver, copper, and aluminum, the second core member is formed from a material selected from the group consisting of tantalum, tungsten, platinum, and platinum-iridium alloys, and the step of processing the composite wire comprises heating the composite wire to a temperature exceeding a melt temperature of the material of the first core member, but not exceeding a melt temperature of the outer member or a melt temperature of the second core member.

7. The method of claim 1, wherein the outer member is formed from stainless steel, the first core member is formed from copper, the second core member is formed from platinum or a platinum-iridium alloy, and the step of processing the composite wire comprises exposing the composite wire to nitric acid.

8. The method of claim 1, wherein the each of the first core member and the second core member is D-shaped in cross-section including a flat side and a rounded side, wherein the respective flat sides of the first and second core members abut each other.

9. A method of a stent comprising the steps of:
shaping a composite wire into a stent pattern, wherein the composite wire comprises an outer member and a dual core member disposed within a lumen of the outer member, wherein the dual core member comprises a first core member disposed within a first portion of the lumen and a second core member disposed within a second portion of the lumen, wherein the second core member comprises a radiopaque material;
processing the composite wire such that the first core member is removed from the lumen of the outer member without adversely affecting the outer member and the second core member, wherein the processing step occurs prior to placement of the stent within a body.

10. The method of claim 9, further comprising the step of filling the first portion of the lumen of the outer member with a biologically or pharmacologically active substance.

11. The method of claim 9, further comprising the step of providing openings through the outer member to the first portion of the lumen of the outer member.

12. The method of claim 9, wherein the outer member is formed from MP35N, the first core member is formed from tantalum, and the second core member is formed from a platinum iridium alloy, wherein the step of processing the composite wire to remove the first core member comprises exposing the composite wire to a xenon difluoride gas.

13. The method of claim 9, wherein the outer member is formed from a material selected from the group consisting of MP35N, L605, 316L stainless steel, the first core member is formed from a material selected from the group consisting of silver, copper, and aluminum, the second core member is formed from a material selected from the group consisting of tantalum, tungsten, platinum, and platinum-iridium alloys, and the step of processing the composite wire comprises heating the composite wire to a temperature exceeding a melt temperature of the material of the first core member, but not exceeding a melt temperature of the outer member or a melt temperature of the second core member.

14. The method of claim 9, wherein the outer member is formed from stainless steel, the first core member is formed from copper, the second core member is formed from platinum or a platinum-iridium alloy, and the step of processing the composite wire comprises exposing the composite wire to nitric acid.

15. A method of forming a stent comprising the steps of:
shaping a composite wire into a stent pattern, wherein the composite wire comprises an outer member and a dual core member disposed within a lumen of the outer member, wherein the dual core member comprises a first core member disposed within a first portion of the lumen and a second core member disposed within a second portion of the lumen, wherein the first core member is disposed outside of the second core member;
processing the composite wire such that the first core member is removed from the first portion of the lumen of the outer member without adversely affecting the outer member and the second core member such that the first portion of the lumen of the outer member is outside of the second core member, wherein the processing step occurs prior to placement of the stent within a body.

16. The method of claim 15, wherein the second core member comprises a radiopaque material.

17. The method of claim 15, further comprising the step of filling the first portion of the lumen of the outer member with a biologically or pharmacologically active substance.

18. The method of claim 15, further comprising the step of providing openings through the outer member to the first portion of the lumen of the outer member.

19. The method of claim 15, wherein the outer member is formed from MP35N, the first core member is formed from tantalum, and the second core member is formed from a platinum iridium alloy, wherein the step of processing the composite wire to remove the first core member comprises exposing the composite wire to a xenon difluoride gas.

20. The method of claim 15, wherein the outer member is formed from a material selected from the group consisting of MP35N, L605, 316L stainless steel, the first core member is formed from a material selected from the group consisting of silver, copper, and aluminum, the second core member is formed from a material selected from the group consisting of tantalum, tungsten, platinum, and platinum-iridium alloys, and the step of processing the composite wire comprises heating the composite wire to a temperature exceeding a melt temperature of the material of the first core member, but not exceeding a melt temperature of the outer member or a melt temperature of the second core member.

21. The method of claim 15, wherein the outer member is formed from stainless steel, the first core member is formed from copper, the second core member is formed from platinum or a platinum-iridium alloy, and the step of processing the composite wire comprises exposing the composite wire to nitric acid.

22. The method of claim 15, wherein the each of the first core member and the second core member is D-shaped in cross-section including a flat side and a rounded side, wherein the respective flat sides of the first and second core members abut each other.

\* \* \* \* \*